United States Patent [19]
Joshi et al.

[11] Patent Number: 6,034,085
[45] Date of Patent: Mar. 7, 2000

[54] SALT FORM OF NEFAZODONE FOR USE IN EXTENDED RELEASE FORMULATIONS

[75] Inventors: Hemant N. Joshi, Dayton, N.J.; Terry D. Wilson, Albany, N.Y.; Jatin M. Patel, Lawrenceville, N.J.

[73] Assignee: Bristol-Myers Squibb Co., Princeton, N.J.

[21] Appl. No.: 09/161,698

[22] Filed: Sep. 29, 1998

Related U.S. Application Data

[63] Continuation-in-part of application No. 08/333,390, Nov. 2, 1994.

[51] Int. Cl.⁷ ........................ A61K 31/495; C07D 403/06
[52] U.S. Cl. ............................................. 514/252; 544/366
[58] Field of Search .............................. 544/366; 514/252

[56] References Cited

U.S. PATENT DOCUMENTS

| | | | |
|---|---|---|---|
| 3,381,009 | 4/1968 | Palazzo et al. | 544/362 |
| 4,338,317 | 7/1982 | Temple et al. | 514/252 |
| 4,487,773 | 12/1984 | Temple et al. | 514/252 |
| 4,910,196 | 3/1990 | Terni et al. | 514/224.5 |
| 5,188,836 | 2/1993 | Muhammad et al. | 424/439 |

FOREIGN PATENT DOCUMENTS

WO94/18978  9/1994  European Pat. Off. .

OTHER PUBLICATIONS

Agharkar, et al., "Enhancement of Solubility of Drug Salts by Hydrophilic Counterions: Properties of Organic Salts of an Antimalarial Drug," *Journal of Pharmaceutical Sciences*, vol. 65, No. 5, May 1976, pp. 747–749.

*Primary Examiner*—Emily Bernhardt
*Attorney, Agent, or Firm*—Richard P. Ryan

[57] ABSTRACT

The crystalline, stable methanesulfonate salt of nefazodone showed significantly higher intrinsic dissolution in water and THAM buffer (pH 7.5) compared to other salts of nefazodone. The faster dissolution rate of this salt at neutral pH suggests better dissolution and absorption in the intestine, allowing controlled release of nefazodone for oral formulations.

3 Claims, 4 Drawing Sheets

SALT FORM OF NEFAZODONE FOR USE IN EXTENDED RELEASE FORMULATIONS

CROSS REFERENCE TO RELATED APPLICATION

This continuation-in-part application claims the benefit of U.S. application Ser. No. 08/333,390 filed Nov. 2, 1994.

BACKGROUND OF THE INVENTION

The present invention relates to an improved salt form of nefazodone, an antidepressant agent. The improved salt form of this invention is a stable solid having improved dissolution characteristics throughout the gastrointestinal pH range.

Temple and Lobeck in U.S. Pat. No. 4,338,317 describe the preparation of nefazodone and analogs, their use as antidepressants, and certain acid addition salts thereof, particularly the hydrochloride salt. Specifically, Temple and Lobeck describe conversion of nefazodone and analogs to pharmaceutically acceptable acid addition salts by conventional methods. The term "pharmaceutically acceptable acid addition salts" referred to salts formed from mineral acids such as hydrochloric, hydrobromic, hydroiodic, nitric, and phosphoric acids and from organic acids such as acetic, citric, palmitic, benzoic, mandelic, mucic, isethionic, and heptanoic.

Nefazodone as the hydrochloride salt is the selected form used as the active ingredient in the prescription antidepressant product SERZONE®. Nefazodone has $pk_a$ values of about 6.4 and 9.5 and demonstrates low aqueous solubility at pH values greater than 6. Bioavailability studies directed to extended release pharmaceutical forms of nefazodone HCl suggest that the low observed bioavailability of nefazodone in extended release formulations is attributable to the low solubility of nefazodone hydrochloride in the intestinal tract where the pH ranges from about 5–7.

While aqueous solubilities differ for various salt forms of drug bases, such as nefazodone, simple aqueous solubility data by itself may be only one of several factors contributing to the bioavailability of a drug. Another factor may be the effect of pH on solubility. Where limited bioavailability is mainly due to lack of simple aqueous solubility, selection of a more water-soluble salt form can raise the drug's bioavailability. Drug solubility in aqueous solution is often a very important criterion for I.V. formulations.

Agharkar, et al. reported in the *Journal of Pharm. Sci.*, 65/5 (May 1976), pp.747–749 that organic acid salt forms of basic drugs have higher aqueous solubilities than their corresponding halide salts. One objective of Agharkar's work was to enhance solubility of an antimalarial drug sufficiently so that parenteral administration would be feasible. At the present time Agharkar's observation is, at best, a rule of thumb as numerous exceptions to this general observation exist.

There can be several pharmaceutical strategies for enhancing drug absorption from a dosage formulation as it travels through the gastrointestinal tract. Most of these utilize special pharmaceutical formulations, with or without salt form modification, and are usually intended for use as extended release medicaments.

An example of these is described by Muhammed, et al. in U.S. Pat. No. 5,188,836 wherein a semi-enteric controlled release formulation allows absorption in both the acidic stomach environment and the neutral conditions of the small intestine. The formulation relies on use of a combination of coating materials that become soluble at different points in the digestive tract. This patent does not deal with different salt forms.

An objective of the present invention was to find a nefazodone salt that could be formulated as an extended release oral dosage form. Selection of a salt form for nefazodone that would overcome the solubility problem in the neutral environment of the small intestine is certainly not predictable beforehand. For extended release the salt should exhibit solubility under pH conditions of the small intestine as well as being bioavailable in the acidic gastric environment of the stomach. In addition, such a salt must be pharmaceutically acceptable, readily characterizable, stable under pharmaceutical processing and storage conditions, and present no special problems in handling or formulating.

There is no teaching in the prior art that would lead beforehand to selection of the methanesulfonate salt of nefazodone as a salt meeting the aforementioned criteria for incorporation into a controlled release dosage form of nefazodone.

SUMMARY OF THE INVENTION

The methanesulfonate (mesylate) salt of nefazodone overcomes bioavailability problems caused largely by nefazodone's poor solubility in the intestinal environment. In addition, the mesylate salt is a stable solid presenting no problems during pharmaceutical handling and storage. The mesylate salt of nefazodone will allow the development of extended release dosage formulations of nefazodone wherein significant absorption from the small intestine is required.

DETAILED DESCRIPTION OF THE INVENTION

The invention deals with selection of the methanesulfonate (mesylate) salt of nefazodone as a salt form possessing characteristics that would allow its use in extended release formulations. Essentially, nefazodone mesylate appears to provide solubility in both gastric and intestinal environments, thereby allowing absorption as it travels through the gastrointestinal tract following administration of an oral dosing form such as a tablet or capsule.

Prior formulation work with nefazodone as the hydrochloride salt indicated a problem with limited solubility in the more neutral pH range of aqueous media. Earlier bioavailability study of nefazodone in extended release pharmaceutical formulations indicated that nefazodone release was inhibited in the human intestinal tract where the pH approaches neutrality. Various salts of nefazodone were prepared and studied. The mesylate salt of nefazodone was selected as the salt of choice for use in extended release formulations. Not only did the mesylate exhibit solubility throughout the gastrointestinal tract but was also readily prepared, reliably characterized and found to be stable under conditions of pharmaceutical processing and storage.

Table 1 sets out intrinsic dissolution rates for various salts of nefazodone in water at 37° C. The final pH value is the pH of the aqueous medium after dissolution had occurred. Nefazodone's solubility is generally enhanced by acidic pH and nefazodone salt solubilities where the final pH is in the range above 5 seem to bear this out. Low solubilities are observed for nefazodone base, and the succinate and acetate salts. Note, however, that the tosylate salt's dissolution rate is also slow even though the media is acidic in nature.

TABLE 1

Melting Points and the Intrinsic Dissolution Rates (n = 2) of Various Salts of Nefazodone in Water at 37° C. Melting Points were Obtained from Differential Scanning Calorimetry.

| Salt | Dissolution Rate (mg/min/cm$^2$) | Final pH | Melting Point, ° C. |
|---|---|---|---|
| Nefazodone base | 0.002 | 7.2 | 82.4 ± 1.1 |
| Hydrochloride | 0.93 | 4.4 | 180 |
| D-Malate | 1.15 | 4.2 | 105 |
| DL-Malate | 0.98 | 4.3 | 108 |
| L-Malate | 1.36 | 4.2 | 116 |
| D-Tartrate | 1.13 | 3.7 | 93 |
| DL-Tartrate | 1.2 | 3.7 | 84 |
| L-Tartrate | 0.97 | 3.8 | 94 |
| Mesylate | 2.7 | 4.0 | 158 |
| Tosylate | 0.1 | 4.4 | 159 |
| Maleate | 0.30 | 4.8 | 150 |
| Succinate | 0.16 | 5.0 | 98 |
| Acetate | 0.03 | 5.4 | 76 |

Figure 1:
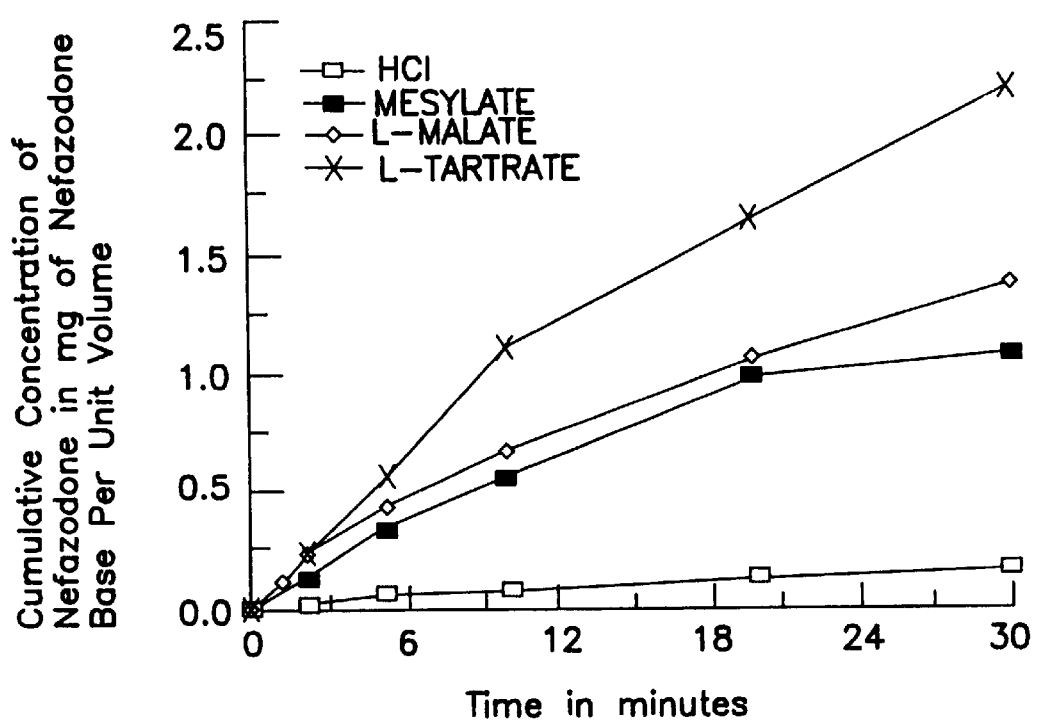
FIG. 1 shows the dissolution profiles of several salts of nefazodone (in powdered form) in 0.125M tri(hydroxymethyl)aminomethane (THAM) buffer solution (pH 7.5 at 37° C.). The curves are plotted as cumulative amounts of nefazodone versus time in minutes.

To assess solubility in non-acidic media, dissolution rates were determined for selected nefazodone salts in THAM buffer (0.125M, pH 7.5) made by dissolving tri (hydroxymethyl)aminomethane in water and adjusting the pH with conc. hydrochloride acid. The dissolution profiles shown in FIG. 1 demonstrate several-fold higher concentrations of drug for several salts compared to the hydrochloride salt of nefazodone. While in the higher grouping, the mesylate is not the best of those shown.

Remaining dissolution experiments were made with the nefazodone salts formulated into tablets as described more fully infra. Essentially, the tablets were comprised of a nefazodone salt, hydroxypropylcellulose, lactose and magnesium stearate.

Figure 2:
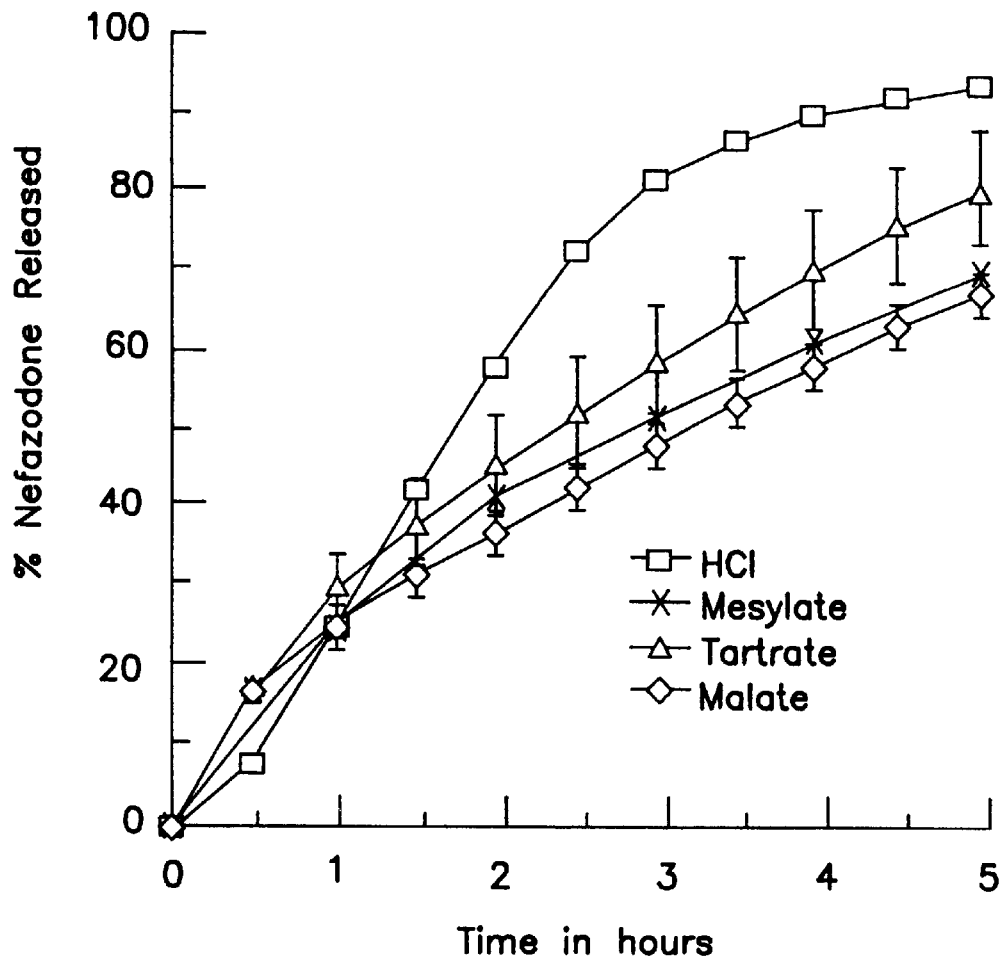
FIG. 2 shows dissolution profiles of nefazodone salts from tablets placed in simulated gastric fluid (pH 1.2 at 37° C.). The curves are plotted as percent nefazodone released over time in hours.

In FIG. 2 drug release from these tablets from a simulated gastric fluid media (pH 1.2 at 37° C.) is shown. The hydrochloride salt demonstrates good solubility in this environment whereas the mesylate salt tablet gives more modest release.

Figure 3:
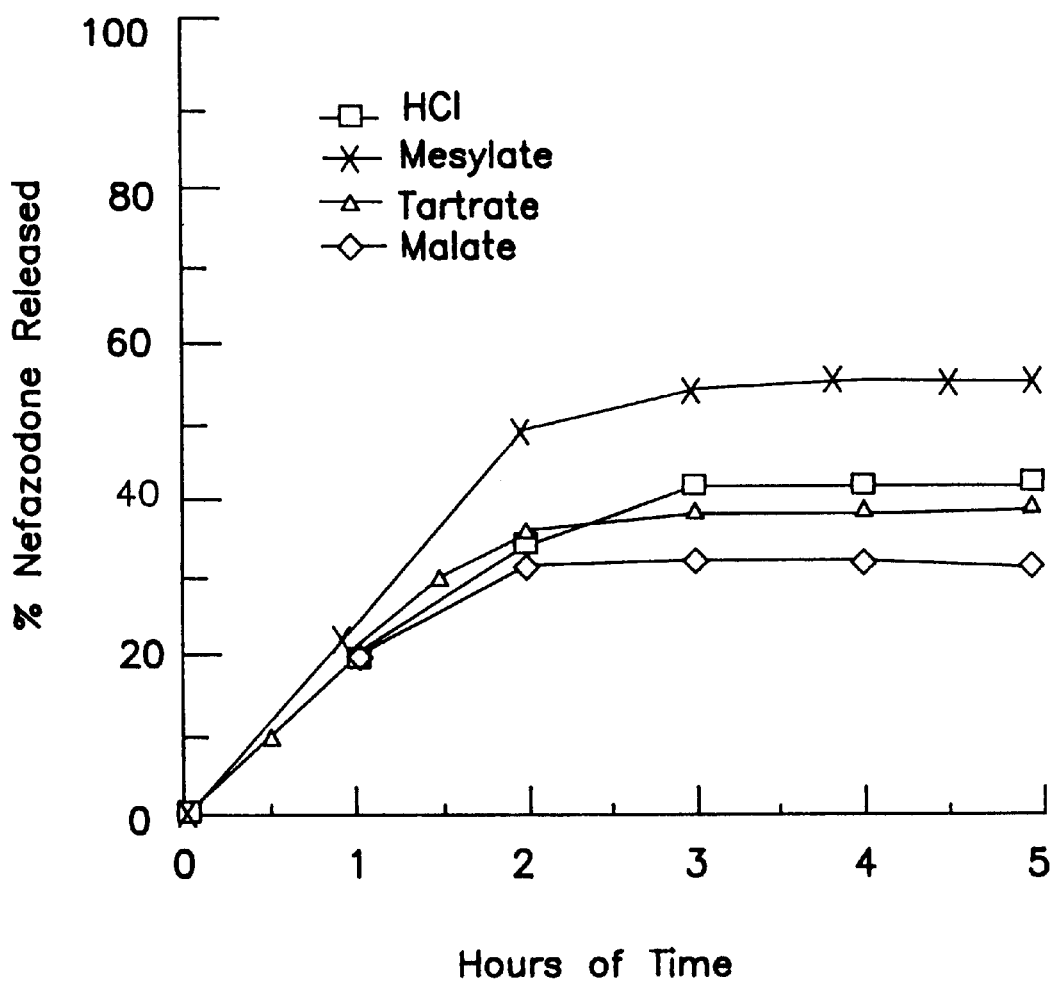
FIG. 3 shows dissolution profiles of nefazodone salts from tablets placed in simulated intestinal fluid (pH 7.5 at 37° C.). The curves are plotted as percent nefazodone released over time in hours.

FIG. 3 displays drug release from the same tablet forms from simulated intestinal fluid (pH 7.5 at 37° C.). The mesylate salt performs better than the other salts.

Figure 4:
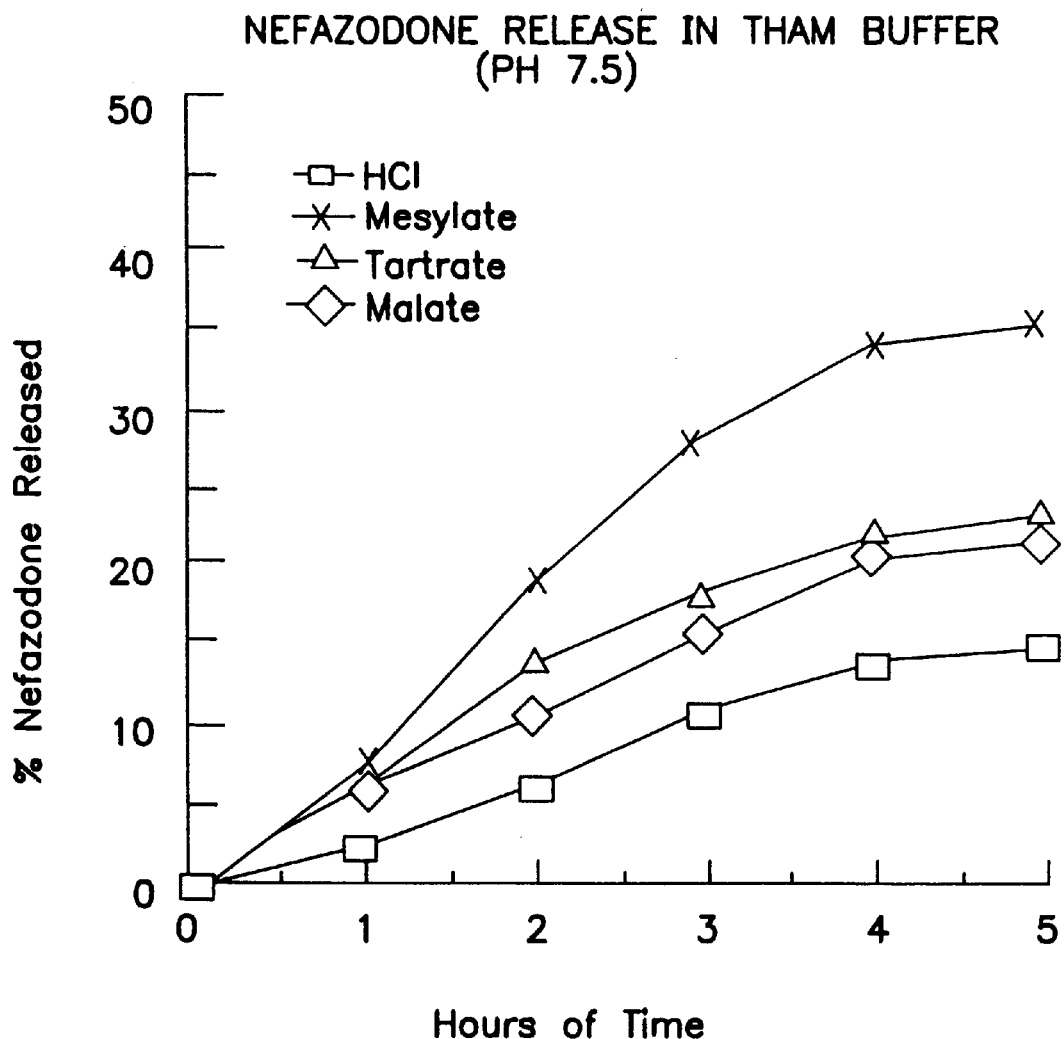
FIG. 4 shows dissolution profiles of nefazodone salts from tablets placed in 0.5M THAM buffer (pH 7.5 at 37° C.). The curves are plotted as percent nefazodone released over time in hours.

In FIG. 4 the tablet forms are studied in 0.5M THAM buffer at pH 7.5, 37° C. Here again the mesylate salt outperforms the others.

Taken together, the above experiments indicate that the dissolution properties of nefazodone mesylate in a tablet pharmaceutical formulation has a superior profile for use in controlled/extended release oral pharmaceutical dosage forms. The good but not excessive dissolution of the mesylate in simulated gastric conditions coupled with its best of class dissolution in simulated intestinal media give nefazodone mesylate a superior continuing dissolution profile for transit via the gastrointestinal tract following oral administration. That is, nefazodone mesylate will be released from an oral dosage form continuously as it passes through the entire gastrointestinal system.

As mentioned previously, other criteria must also be satisfied to select a salt of nefazodone for use in extended release formulations. Ease of preparation, appearance, reliability of characterization, ease of handling and formulating, and the salt's stability are other factors to be considered. In studying additional salt forms of nefazodone, certain salts were difficult to obtain in crystalline form such as the acetate, the L- and DL-lactates, and ethanesulfonamide; others, such as the citrate salt had low melting points that would be problematic in pharmaceutical processing. Other salts could not be solidified; e.g., nefazodone lactate, nefazodone adipate and nefazodone phosphate. While these unsuitable characteristics could not be predicted beforehand, their presence eliminated these salts from consideration.

New salts of nefazodone were prepared by contacting commercially available acids; e.g., malic, tartaric and methane sulfonic acids with nefazodone base under suitable conditions. The resultant salts were then incorporated into pharmaceutical compositions and studied for feasibility for delivering nefazodone to subjects in an extended/controlled release fashion.

The invention also deals with the administration of nefazodone mesylate via orally-ingested dosage forms. Thus tablets, capsules, caplets, lozenges, suspensions, and the like are suitable forms. The use of tablets is preferred.

The oral pharmaceutical compositions may contain a variety of conventional pharmaceutically acceptable excipients in effective amounts suitable for their respective functions. Thus, suitable amounts of conventional additives, such as the following, are useful: polymeric matrixes (e.g., chitosan, hydroxyalkylcelluloses), auxiliary binding agents (e.g., syrup, acacia, gelatin, sorbitol, tragecanth, or polyvinyl pyrrolidone), fillers (e.g., lactose, sugar, maize-starch, calcium phosphate, sorbitol or glycine), lubricants (e.g., magnesium stearate, cellulose, talc, polyethyleneglycol or silicas), disintegrants (e.g., starch), wetting agents (e.g., sodium lauryl sulfate), colorants (e.g., iron oxides), etc. Mixtures can be used.

Generally, the pharmaceutical compositions of the invention will contain from about 20 to about 50% wt % of nefazodone mesylate as the active pharmaceutical agent and from about 80 to about 50 wt % of pharmaceutically acceptable carrier(s) such as release extending agents and other excipients.

Effective doses of nefazodone mesylate of from about 0.01 to about 40 mg/kg body weight are contemplated. Generally, about 200 to about 300 mg/day are given. Dosage levels may vary according to the medical needs of the subject, (e.g., the human patient or other host). In any event, sound medical judgment, such as that exercised by a licensed physician, should be used in determining optimal dosages.

The compositions and dosage forms discussed herein are designed to deliver an effective antidepressant amount of nefazodone mesylate to a mammal, preferably a human patient.

Reasonable variations, such as those which would occur to a skilled artisan, can be made herein without departing from the scope of the invention.

Unless stated otherwise, all percentages recited herein are weight percents, based on total composition weight. All references recited are hereby incorporated by reference.

EXAMPLES

The following examples set forth the preparation of nefazodone base and the derivation of the various nefazodone salts.

Example 1 describes the preparation of nefazodone base and the salts discussed herein. Example 2 sets out intrinsic dissolution and release studies conducted using the salts and tablet formulations, respectively.

Example 1: Preparation of Nefazodone Salts

A. Nefazodone Base

Nefazodone HCl was prepared in accordance with Example 2 of U.S. Pat. No. 4,338,317. Nefazodone HCl was dissolved in water with gentle heating (40–45° C.). An equimolar quantity of sodium hydroxide solution (0.1 N) was added with constant stirring while cooling with ice. Nefazodone base precipitated as a sticky gum which was separated and washed repeatedly with water. The base was washed with water until no chloride ions ($AgNO_3$ test) were detected in the washings. Nefazodone base was then dissolved and crystallized from isopropyl alcohol (IPA) to give a solid melting 81–83° C.

B. Nefazodone Salts

Nefazodone base (1 gram) was dissolved in 6–8 mL of isopropyl alcohol (IPA) with gentle heating. Selected acids (1.05 mole equivalent) were dissolved in 2 mL of IPA. The two solutions were mixed and stirred thoroughly with stirring. In most instances, the salt precipitated immediately and was filtered and washed well with IPA.

C. Nefazodone Mesylate

Using the above procedure with appropriate selection of starting materials, nefazodone mesylate was prepared and could be purified by recrystallization in alcohol (MeOH, EtOH, i-PrOH). When water was present during the alcohol recrystallization process, a hydrate of the mesylate salt is apparently formed which melts at 110° C.

Example 2: Dissolution and Release Studies

The intrinsic dissolution experiments were performed with 75 mL water as the dissolution medium. The details of these dissolution experiments are summarized below:

Container: Double-walled beaker, 100 mL capacity, round bottom.

Temperature: 37° C.

Volume of sample withdrawn per interval: 1 mL.

Temperature of the solution in the beaker was maintained by means of a circulating waterbath. The medium was stirred with a USP II paddle using 100 rpm stirring rate (paddle depth=1 inch below the surface of the medium). Samples were withdrawn through a 0.45 µm syringe filter and were analyzed without any further dilution or treatment by HPLC (Method 1).

Intrinisic Dissolution Experiments in THAM

THAM buffer was prepared by dissolving tri(hydroxymethyl)aminomethane in water and adjusting the pH with concentrated hydrochloric acid. Dissolution of salts of nefazodone in powder form was studied in this medium.

The experiments were conducted in 0.125 M THAM (pH 7.7) at 37° C. using the USP II dissolution apparatus. Nefazodone acids in powder form (about 75–80 mg) were added to 900 mL dissolution medium stirred at 50 rpm and samples were withdrawn at time points up to 2 hours. The USP official method recommends paddles to be 1 inch from the bottom. In this experiment, paddles were ¾ inch from the bottom. The paddle depth was altered to facilitate suspension of the powder during experiments. Samples were analyzed using HPLC assay.

Release Profiles from the Tablet Formulation

The preparation and characterization of tablets of salts of nefazodone was performed as described below:

Ingredients used in the tablets of salts of nefazodone are listed in Table 2.

TABLE 2

Tablet Formulations with Nefazodone Salts Listing Various Ingredients Used

| Ingredient | Amount, mg | |
|---|---|---|
| | Range | Preferred |
| Nefazodone Salt* | 40–60 | 50 |
| Hydroxypropyl Cellulose EF | 10–90 | 50 |
| Lactose | 10–90 | 50 |
| Magnesium Stearate | 0.01–5 | 1 |

*Weight of salt was 50 mg in each formulation. The % dissolved values were calculated.

The nefazodone salt, hydroxypropyl cellulose EF and lactose were mixed for 10–15 minutes. Magnesium stearate was added to this mixture, mixing it for five more minutes. Tablets were compressed using a Manesty machine (Model-Manesty B3B). The tablet hardness was approximately 7 SCU.

Dissolution studies were performed with a USP II apparatus in simulated gastric fluid (USP, pH 1.2), simulated intestinal fluid (USP, pH 7.5) and 0.5 M THAM (pH 7.7). The details of conditions for the dissolution experiments are as follows:

Volume of the medium withdrawn at each interval: 900 mL.

Sample volume withdrawn at each interval: 0.7 mL.

Temperature: 37° C.

Stirring speed: 50 rpm.

Samples were filtered during withdrawal and chromatographed without further dilution or treatment. Samples were analyzed by Waters HPLC system. The HPLC conditions are listed in Method 2 below.

HPLC Conditions

Method 1

Column: Novapak, C18, 7.5 cm

Mobile Phase: ACN:water:diethyl amine (600:400:0.5 v/v)

Wavelength: 254 nm

Flow rate: 1.25 mL/min

Retention time: 2.2 minutes

Injection volume: 20 µL

Method 2

Column: µ Bondapak, C18, 15 cm

Mobile Phase: Methanol:0.01 M Ammonium Phosphate buffer, pH 6.0 (85:15, v/v)

Wavelength: 254 nm

Flow rate: 1.0 mL/min

Retention time: 2.5 minutes

When SCF was used as the dissolution medium, Method 2 was slightly modified. Methanol:buffer ratio in the mobile phase was 75:25 and the flow rate was 1.2 mL/min.

What is claimed is:

1. Nefazodone mesylate.

2. A pharmaceutical composition useful for orally administering nefazodone mesylate which contains:

a) an effective antidepressant amount of nefazodone mesylate and b) a suitable amount of a pharmaceutically acceptable carrier.

3. A method of controlling the release of nefazodone comprising administering to a patient in need thereof an oral dosage form containing nefazodone mesylate.

* * * * *